United States Patent [19]

Skiles et al.

[11] Patent Number: 5,166,154
[45] Date of Patent: Nov. 24, 1992

[54] IMIDAZO[1,2-A]PIPERAZINES

[75] Inventors: Jerry W. Skiles, Brookfield; Victor Fuchs, New Fairfield, both of Conn.

[73] Assignee: Boehringer Ingelheim Pharmaceuticals, Inc., Danbury, Conn.

[21] Appl. No.: 726,472

[22] Filed: Jul. 8, 1991

Related U.S. Application Data

[63] Continuation of Ser. No. 422,868, Oct. 17, 1989, abandoned.

[51] Int. Cl.$^5$ ............... C07D 487/04; A61K 31/495
[52] U.S. Cl. .................... 514/249; 514/250; 544/343; 544/346; 544/350
[58] Field of Search ............... 544/350; 514/249

[56] References Cited

PUBLICATIONS

CA 79(23): 137487q (1973).
CA 85(19): 143466x (1976).
CA 95(1): 7741n.

Primary Examiner—Mukund J. Shah
Assistant Examiner—Jyothsna Venkat
Attorney, Agent, or Firm—D. E. Frankhouser; M-M. Timbers; A. R. Stempel

[57] ABSTRACT

Imidazo-[1,2-a]piperazines, inhibitors of human neutrophil elastase, having the following general structure

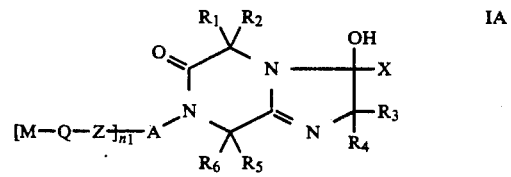

or

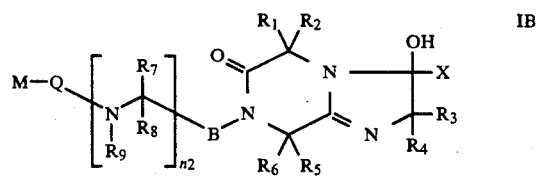

wherein the substituents are defined hereinbelow, are disclosed.

2 Claims, No Drawings

IMIDAZO[1,2-A]PIPERAZINES

This is a continuation of prior application Ser. No. 422,868, filed on Oct. 17, 1987, now abandoned.

This invention relates to new chemical compounds having valuable pharmaceutical activities. In particular the present invention relates to certain imidazo[1,2-a]piperazines derivatives which are inhibitors of human neutrophil elastase (HNE), which property makes such compounds useful whenever such inhibition is desired. For example, such compounds may be useful in the treatment of tissue degenerative disease. Such inhibitors can be used in the diagnosis and treatment of pulmonary emphysema, rheumatoid arthritis, or osteoarthritis, and arteriosclerosis, among other diseases. The substituted imidazo[1,2-a]piperazines of the present invention may be represented by the following formulae

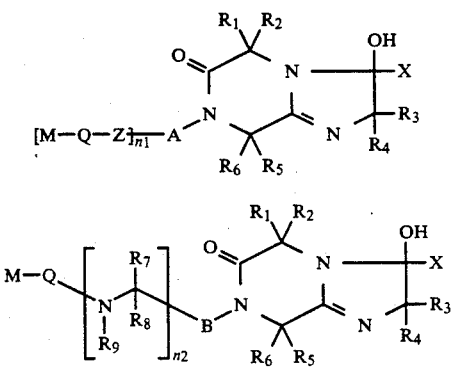

wherein

X is lower alkyl, aryl, nitroalkyl, cyanoalkyl, trihalomethyl, $C(halo)_2CO_2R$, aralkyl, where R is lower alkyl or $C_1$-$C_8$ aralkyl, and the aryl groups may optionally be substituted with groups such as halogen, nitro, $C(halogen)_{n3}$, $C(halogen)_{n3}CO$, cyano, lower alkyl or $SO_3H$, where $n_3$ is the integer 1, 2 or 3.

B is $CR_1R_2$, CO, a chemical bond, or equivalent to A as described below but not hydrogen $n_1$ is the integer 0 or 1

$n_2$ is the integer 0, 1 or 2

A is hydrogen, alkyl, alkenyl, cycloalkyl, cycloalkyl-alkyl, polycycloalkyl, polycycloalkyl-alkyl, aryl, aralkyl, heteroaryl, alkynyl, acyl, heteroaryl-alkyl, heterocycloalkyl, heterocycloalkyl-alkyl, fused polycyclic aryl, fused cycloalkyl-aryl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkyl-amino-alkyl, dialkyl-aminoalkyl, indanyl, alkanoyl, aryloyl or alkylheteroalkyl.

$R_1$, $R_2$, $R_3$, $R_4$, $R_5$, $R_6$, $R_7$ and $R_8$ are each selected from hydrogen, lower alkyl, substituted alkyl, aryl, heteroaryl-alkyl, heterocycloalkyl-alkyl, cycloalkyl-alkyl, aralkyl, substituted aralkyl, or substituted aryl.

$R_1$, $R_2$, $R_3$, $R_4$, $R_5$, $R_6$, $R_7$ and $R_8$ may also be obtained from the side chains of naturally occurring alpha-amino acids. $R_1$, $R_2$, $R_3$, $R_4$, $R_5$, $R_6$, $R_7$ and $R_8$ may be lower alkyl groups containing from 1 to 12 carbons and may be substituted by the following groups: hydroxy, alkoxy, amino, alkyl-heteroalkyl, alkylamino containing from 1 to 6 carbons, dialkylamino wherein each alkyl group contains from 1 to 6 carbons, alkanoyl containing from 1 to 6 carbons, arylcarbonyl wherein the aryl group contains 6, 10, or 12 carbons, aralkanoyl containing 8 to 13 carbons, amido which may be attached to the alkyl group via either the nitrogen or carbon of the amido or guanidino, carboxy, carboxy lower alkyl, cycloalkyl (3-15 carbons), cycloalkyl-alkyl (4-12 carbons), heteroaryl, aryl which may optionally be partially hydrogenated, heteroarylalkyl, aryl containing 6, 10 or 12 carbons, bicycloalkyl, bicycloalkyl-alkyl, alkylureido, aralkylureido, arylureido; fused arylcycloalkyl, or the substituent-A as defined above.

$R_9$ is hydrogen, lower alkyl, aralkyl, or cycloalkyl

Q is selected from the group consisting of

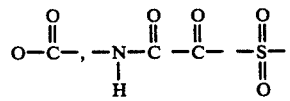

M is alkyl, substituted alkyl, cycloalkyl, substituted cycloalkyl, alkenyl, substituted alkenyl, aryl, substituted aryl, aralkyl, substituted aralkyl, an aliphatic heterocycle, an aromatic heterocycle or a substituted aromatic heterocycle.

In particular, M is preferably selected from one of the following:

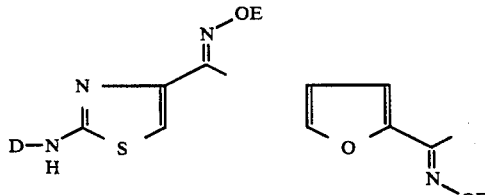

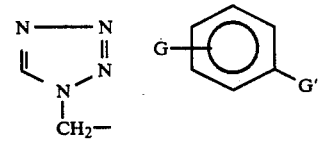

wherein

D is hydrogen, lower alkyl (1 to 12 carbons), alkanoyl (1 to 12 carbons), aryl, and aryloyl (1 to 12 carbons). When D is alkyl or alkanoyl it may optionally be substituted by branched or non-branched lower alkyl groups, aryl groups, carboxy, carboxy lower alkyl, amino, aminoalkyl, dialkylamino, hydroxy, or alkoxy groups. The aryl groups may optionally be substituted by halogen, nitro, carboxy, alkyl, alkoxy, $SO_3H$, $CF_3$, $C(halogen)_{n3}$, acetyl, $CF_3CO$, wherein $n_3$ is defined hereinabove.

E is hydrogen, lower alkyl, $C(R_1R_2)COOR$, wherein R, $R_1$, and $R_2$ are defined hereinabove.

G is hydrogen, lower alkyl, halogen, acetyl, trihaloacetyl, alkanoyl, aryloyl, trihalomethyl; and G' is the group —($SO_2NHCO$) aryl.

A or B and $R_6$ may be connected together to form a saturated or unsaturated bridge of from 2 to 5 carbon atoms; from 2 to 4 carbon atoms and one oxygen or sulfur atom; fused aralkylene; fused cycloalkyl-alkylene; or a bridge as above, or fused aralkylene, substituted with hydroxy, lower alkoxy, or lower alkyl. If sulfur occurs in the ring it may optionally be oxidized to the corresponding sulfoxide or sulfone.

Z is NR, lower alkyl, chemical bond, S, O, $N(CR_1R_2)_{n3}$
wherein $R_1$, $R_2$ and $n_3$ are defined hereinabove.

The alkyl groups per se and in the alkyl moiety in aralkyl, cycloalkyl-alkyl, polycycloalkyl-alkyl, heteroaryl-alkyl and the like, and in alkoxy, alkylthio, alkanoyl, carbalkoxy, and alkylamino, may be straight chained or branched and are preferably lower alkyl groups containing from 1 to 12 carbons. Such groups include methyl, ethyl, propyl, isopropyl, butyl, isobutyl, amyl, iso-amyl, hexyl, and the like.

The alkenyl and alkynyl groups may also be branched or straight-chained and contain from 2 to 10 carbon atoms. Such groups include vinyl, ethynyl, propenyl, allyl, isopropenyl, propyl, butynyl, pentynyl, and the like.

In the definition of the A-substituent, cycloalkyl, poly-cycloalkyl, aryl, heteroaryl, arylalkyl, fused aryl-cycloalkyl groups and the like may contain from 3 to 25 carbon atoms and may carry substituents such as lower alkyl, alkenyl, alkynyl, hydroxy, thio, amino, alkoxy, alkylthio, alkyl-amino, halogen, acetyl, trifluoroacetyl, and nitro. Examples of such A-substituents include such radicals as cyclopropyl, cyclobutyl, cyclopentyl, cyclohexyl, cycloheptyl, norbornyl, adamantyl, phenyl, tolyl, benzyl, cyclooctyl, phenethyl, pyridyl, pyridyl-methyl, idanyl, imidazolyl, furyl, furfuryl, benzimidazolyl, morpholinyl, pyrrolyl, pyrrolidyl, piperidyl, piperazinyl, napthyl, dimethoxyphenethyl, dimethoxyphenyl, quinolyl, isoquinolyl, tetrahydrofuryl, thienyl, tetrahydrothienyl, and the like. In the definition of A-substituents, wherein A is a heterocyclic group, such group may be mono- or polycyclic and include the above groups. The nitrogen in the pyridyl substituent may be oxidized to the N-oxide, and the sulfur in tetrahydrothienyl may be oxidized to the sulfone or sulfoxide.

As will be appreciated by those skilled in the art, the imidazo[1,2-a]piperazines of the present invention may have several asymmetric carbon atoms and thus may exist in several diastereomeric forms. The preferred compounds of the present invention are of the S-configuration which corresponds to the L-configuration of naturally occurring alpha amino acids. The methods of syntheses described herein provide the products as a mixture of diastereomers, based upon the fact that the starting materials are (dl)-mixtures. To those skilled in the art, it is expected that the individual, separated diastereomers may not have the same biological activity (e.g., one may be more active than the other). The present invention contemplates all diastereomeric mixtures as well as the active S and R forms. Additionally, where appropriate the acid and base addition salts thereof may be formed.

As will be appreciated by those skilled in the art, the imidazo[1,2-a]piperazines of the present invention may act as prodrugs of the corresponding open piperazine derivatives 1A and 1B to give IIA and IIB as illustrated below.

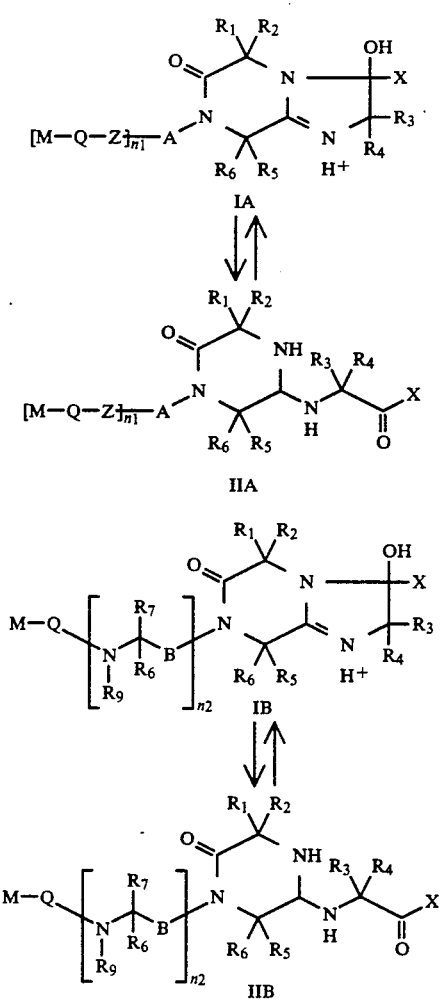

As will also be appreciated by those skilled in the art the open ring piperazine derivatives IIA and IIB may exist as solvates or in particular hydrates as is represented by the structures IIIA and IIIB below

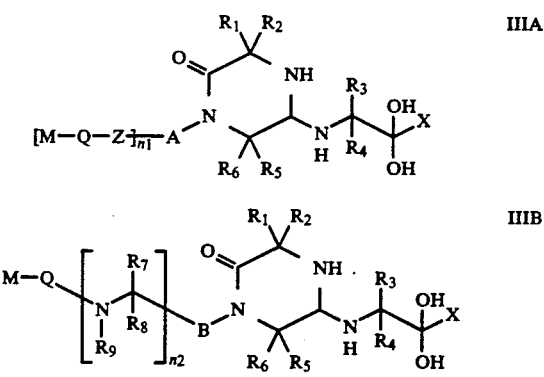

As will also be appreciated by those skilled in the art the imidazole ring of the imidazo[1,2-a]piperazines of the present invention may be dehydrated to afford a second double bond in the imidazole ring as is illustrated by the following formulae. Both structures IVA and IVB are within the scope of the present invention.

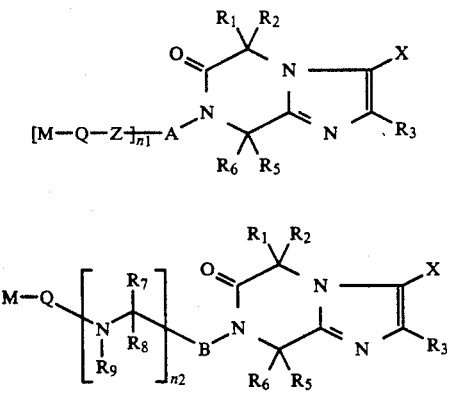

To those skilled in the art it will be appreciated that certain starting materials for the compounds of the present invention are derived from commercially available amino acids, and are obtained from the following: glycine, alanine, valine, leucine, isoleucine, phenylalanine, norleucine, ornithine, tyrosine, tryptophan, glutamine, asparagine, aspartic acid, glutamic acid, lysine, serine, threonine, methionine and sarcosine.

The present invention describes the novel utilization of heterocyclic ring systems such as ring closed imidazo[1,2-a]piperazines and ring opened piperazines to obtain potent and specific inhibitors of HNE. Unlike other known heterocyclic inhibitors of HNE which are irreversible inhibitors, the compounds of the present invention are reversible inhibitors HNE. The compounds in which X is $CF_3$ are the preferred compounds of the present invention.

Scheme A

The natural and non-naturally occurring N-substituted amino acids utilized in the present invention are normally prepared in one of two ways. The first method involves the treatment of an appropriately substituted primary amine 1 with halo- $C(R_6R_5)COOR_{10}$ 2 to give 3. The second method involves the reductive alkylation of an appropriately substituted alpha-amino acid 5 to give 3. To those skilled in the art it is known that the latter reaction may be accomplished by catalytic hydrogenation or by hydride reduction (e.g., $NaCNBH_3$).

SCHEME A

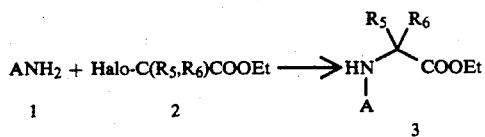

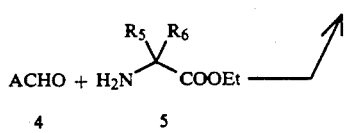

Scheme B

The required trifluoro amino alcohol 8 may be conveniently prepared by three different means: Schemes B, C and D. In Scheme B the appropriately substituted nitro compounds of formula 6 are treated with trifluoroacetaldehyde or with commercially available trifluoroacetaldehyde ethyl hemiacetal of formula $CF_3CH(OH)OCH_2CH_3$ 7 to give the nitro alcohols 8. The trifluoromethyl nitro alcohols 8 are obtained as a mixture of threo and erythro diastereomers. Normally the diastereomers are separated from one another at this stage by chromatography, crystallization, and/or both. The nitro compound 8 is reduced to the amino trifluoroalcohol 9 by a variety of reducing agents which are familiar to those skilled in the art (e.g., $LiAlH_4$, catalytic hydrogenation, etc.). The amine 9 is normally isolated as its hydrochloride salt and is used directly without further purification.

SCHEME B

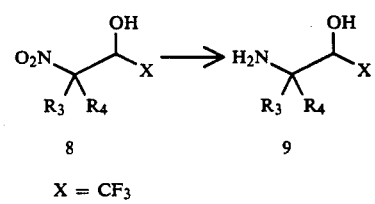

$X = CF_3$

Scheme C

Alternatively the amino trifluoromethyl alcohols 9 may be obtained via a Curtius rearrangement. The synthesis is initiated with the readily available acids 10. The dianion of 10 is generated with lithium diisopropyl amide (LDA) and then treated with trifluoroacetaldehyde to give the alcohol 11. The OH of the acid 11 is treated with TBDMS-OTF(tetrabutyldimethylsilyl triflate) to give the protected alcohol 12. The acid 12 is subjected to a Curtius rearrangement by employing DPPA (diphenylphosphoryl azide) in the presence of benzyl alcohol to give the CBZ-intermediate 13. The silyl protection group of 13 is removed under standard methods familiar to those skilled in the art to give the CBZ-alcohols 14 which are subjected to hydrogenolysis conditions to give the amino alcohols 9.

SCHEME C

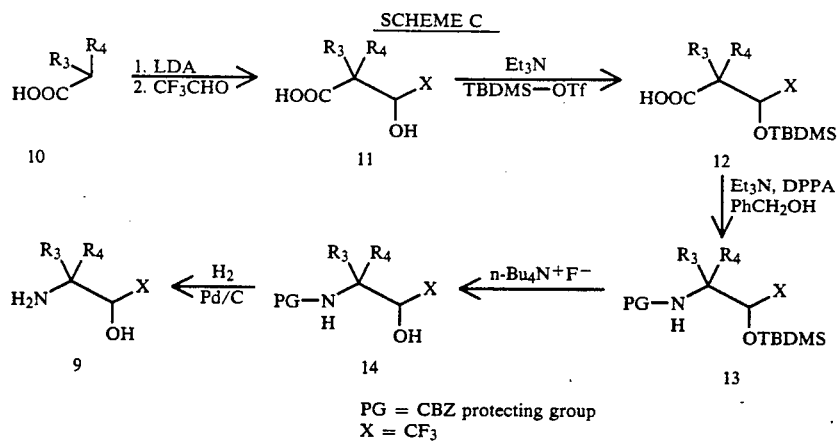

PG = CBZ protecting group
X = CF$_3$

Scheme D

Alternatively, protected amino acids such as 15 (PG=t-BOC; CBZ, or FMOC) is condensed with dimethylhydroxylamine under standard methods familiar to those skilled in the art (e.g., DCC, WSCDI, CDI, mixed anhydride, etc.) to obtain the intermediate aldehydes 16. The amides 16 are reduced with LiAlH$_4$ according to known methods familiar to those skilled in the art to obtain the protected amino acid aldehydes 17. The aldehydes 17 are treated in THF with tetramethyl silane trifluoromethane (TMS-CF3), *J. Amer. Chem. Soc.* 111, 393 (1989), and a catalytic amount of tetrabutyl-ammonium fluoride (D-Bu$_4$N+F−) to give the trifluoromethyl silyl intermediates 18. The trifluoromethyl silyl compounds 18 are deprotected with aqueous hydrogen chloride to give the alcohols 14. The alcohols 14 are subjected to hydrogenolysis conditions, in the case in which PG=CBZ to give the amino trifluoromethyl alcohols 9.

SCHEME E

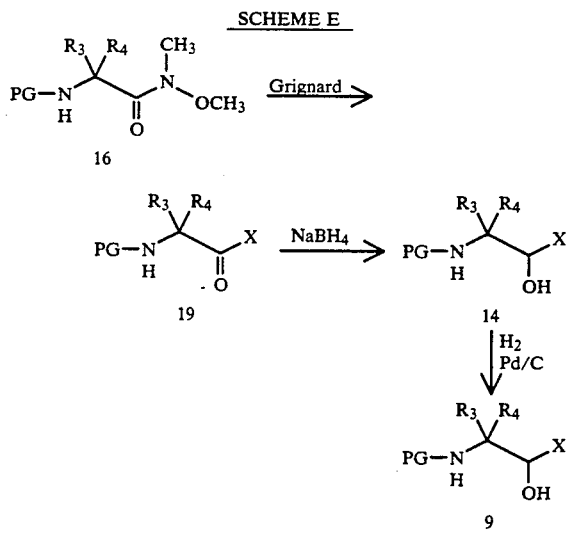

SCHEME D

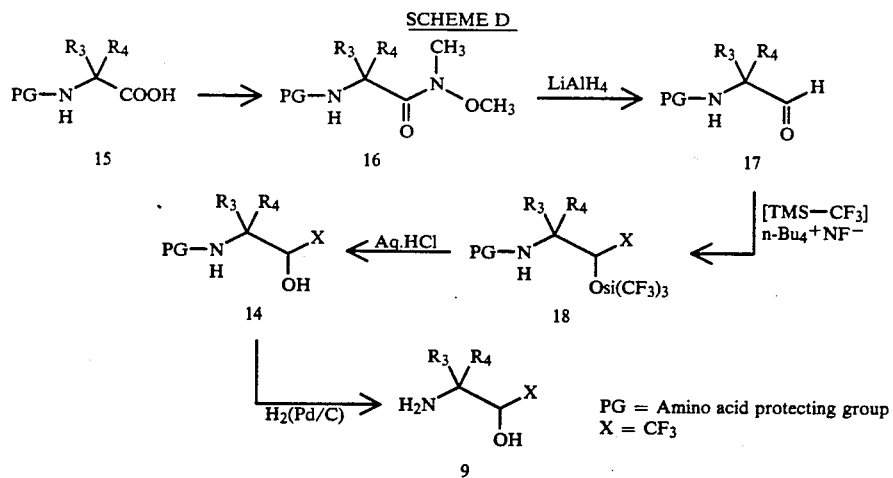

PG = Amino acid protecting group
X = CF$_3$

Scheme E

When X is alkyl or aryl the required protected amino alcohols 9 may be obtained via a Grignard reaction. The amides 16 are treated with the appropriately substituted Grignard reagent to give 19. The ketones may be reduced with NaBH$_4$ to give the alcohols 14 which are then utilized as described in Scheme D above.

Scheme F

The synthesis of the dihalo intermediates such as 21 are prepared ideally according to Scheme B. The N-protected aldehydes 17 are treated under Reformatsky reaction conditions with, for example, BrC(F)$_2$COOEt to give the intermediates 20. The intermediates 20 0are then deprotected by means familiar to those skilled in the art to give the amino-alcohols 21. The amino-alcohols 21 are utilized as described in Scheme G.

SCHEME F

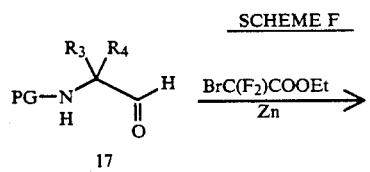

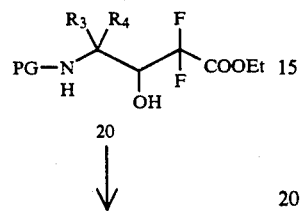

those skilled in the art with the amino alcohols 9 to give 24. The intermediate alcohols 24 are oxidized to provide the ketone peptides 25 by PCC (pyridinium chloroformate), PDC (pyridimium dichromate), oxalyl chloride/DMSO, Jones Reagent, Collins reagent, etc. However, the preferred method of oxidation is by utilization of the Dess-Martin periodinane reagent which is commercially available. The utilization of this reagent has previously been describe [D. B. Dess et al., *Journal of Organic Chemistry*, 48, 4155 (1983)]. The intermediate protected amino ketones 25 are deprotected under standard methods of deprotection familiar to those skilled in the art. In the present invention, for example, commonly used protecting groups for nitrogen can be either CBZ or tert-BOC although others are also contemplated (e.g., FMOC, TROC, etc.). The CBZ intermediates 23 are normally deprotected by catalytic hydrogenolysis or by HBr in acetic acid. The tert-BOC intermediates 23 are deprotected by acid (e.g., hydrogen chloride in p-dioxane).

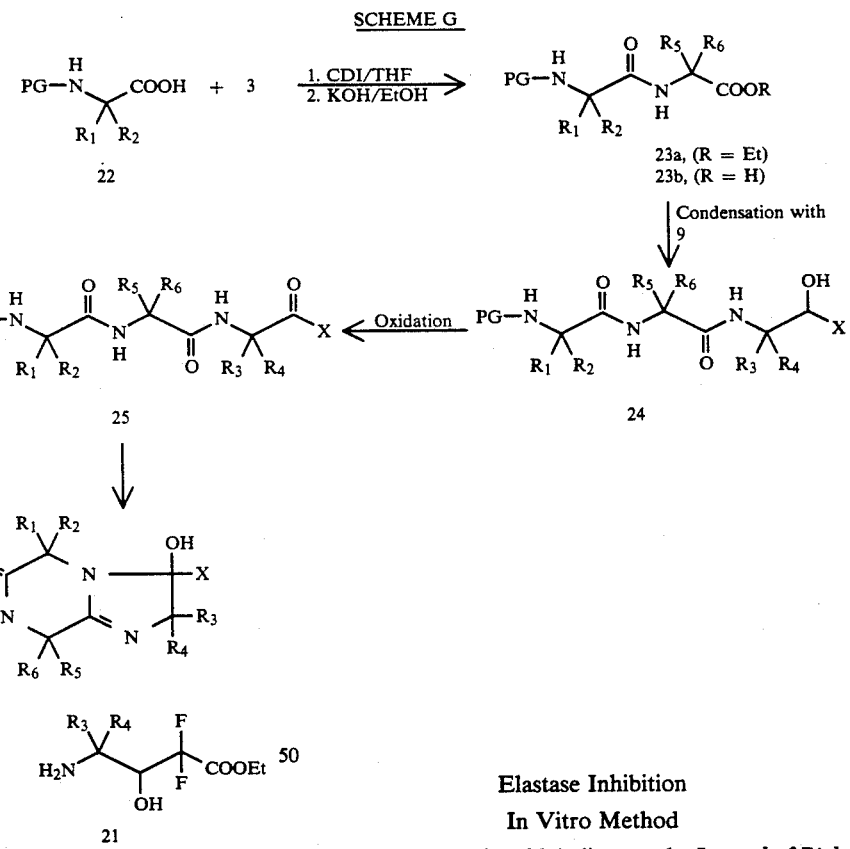

Scheme G

The naturally occurring or non-naturally occurring amino acids 22 are condensed with the appropriately substituted N-protected alpha amino acids 3 according to methods commonly used in peptide synthesis and familiar to those skilled in the art [e.g., M. Bodanszky and A. Bodanszky, "The Practice of Peptide Synthesis", Springer-Verlag, Berlin (1984); M. Bodanszky, "Principles of Peptide Synthesis", Springer-Verlag, Berlin (1984)] to give the dipeptide ester intermediates 23a. The intermediate esters 23a are deprotected under standard methods to give the acids 23b (R=H). The acid 23b is condensed by standard methods familiar to

Elastase Inhibition

In Vitro Method

The method of K. Nakajima et al., *Journal of Biological Chemistry*, 254: 4027–4032 (1979) was adapted to a microtiter format. The in vitro assay is based upon the hydrolysis of the commercially available (Sigma Chemical Company, St. Louis, Mo.) substrate methoxy O-succinyl-L-alanyl-L-alanyl-L-prolyl-L-valine para-nitroanilide (MeO-Suc-Ala-Ala-Pro-Val-pNA) and the release of para-nitroanilide (pNA), which absorbs at 405 nm.

Equipment a. Microtiter plates (96 well, flat bottom)
b. Vmax Kinetic Microtiter Plate Reader, equipped with 405 nm filter (Molecular Devices).
c. Microtiter Plate Mixer (Fisher Scientific)

d. Spectrophotometer (e.g., Cary 118) for Ki and Km determinations

Reagents a. Human sputum elastase (HSE) (Elastin Products Co., Pacific, Mo.) dissolved in 1 mg/mL in 0.05M sodium chloride and frozen (50 μL aliquots) at −20° C. until used.

b. Stock solution of MeO-succinyl-L-Alanyl-L-Alanyl-Pro-Val-pNA dissolved at 15 mM in dimethylsulfoxide (DMSO) and frozen (4 mL aliquots) at −20° C. until used.

c. Assay buffer: 0.1M Tris buffer, pH 7.5 containing 0.5M sodium chloride.

Screening is performed in microtiter plates, using 0.5 mM substrate and monitored on a Microtiter Reader. Enzyme activity (+/− test compound) is determined as the rate of pNA release (linear regression analysis of slope). Inhibitory activity of the test compound is calculated relative to the uninhibited enzyme control, as follows:

$$\% \text{ Inhibition} = \left[ 100 - \frac{\text{rate (with test compound)}}{\text{rate (enzyme control)}} \right]$$

A frozen aliquot of HSE is thawed and diluted with assay buffer to a stock concentration of 0.02 mg/mL (30×assay concentration). A frozen aliquot of the substrate stock solution is thawed and diluted to 0.5 mM with the assay buffer (final DMSO concentration is 10%). 10 μl of the test compound stock solution (or assay buffer) and 10 μl of the HSE stock solutions are pipetted into each microtiter well, in duplicate. The plate is mixed well, and pre-incubated at room temperature for 15 minutes. A 300 μl substrate solution is then added to each well and the OD$_{405}$ is followed for approximately 30 minutes.

Table I sets forth the result of in vitro testing with the compounds of the present invention. Further, it is known to those skilled in the art that the biological activities of pharmaceutical agents may be diminished in vitro when human serum albumin (HSA) is added. This is due to the probable binding of compounds to protein. In the case of the present invention, however, the compounds of the present invention are just as active in vitro without or with 0.5% HSA and thus would be expected not to bind to plasma in an in vivo situation or in a diagnostic setting. The results are set forth in the Table below.

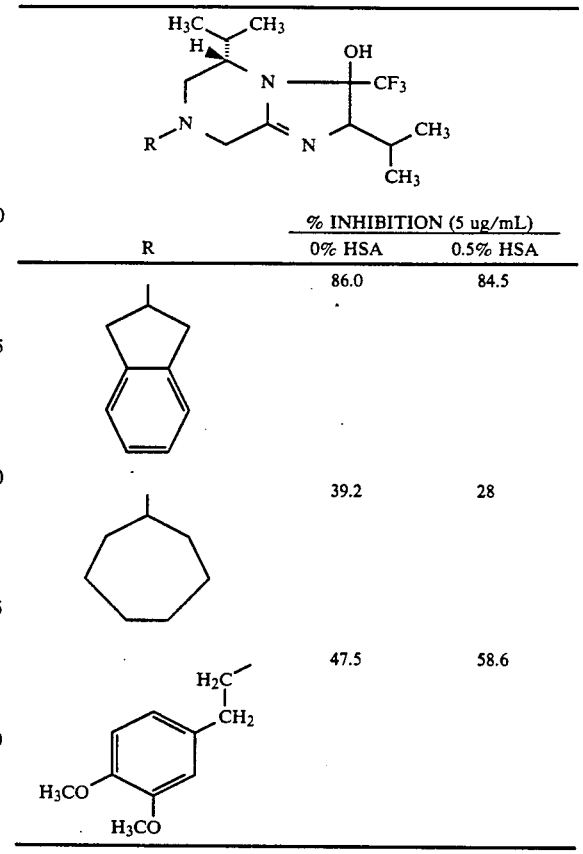

The compounds of the present invention may be administered for the alleviation of conditions which include tissue degenerative diseases such as: pulmonary emphysema, artherosclerosis and osteo- and rheumatoid arthritis, in particular emphysema, and other diseases. The mode of administration may be parenteral, including the subcutaneous deposit by an osmotic pump, or via a powdered or liquid aerosol. For parenteral administration, an intravenous, intramuscular, or subcutaneous injection would be given containing 0.02 to 10 mg/kg of a compound of the invention two or four times daily. The injection would contain a compound of the invention in a aqueous isotonic sterile solution or optionally a suspension with a preservative such a phenol or a solubilizing agent such as ethylenediamine tetra-acetic acid (EDTA), and an aerosol. Compounds of the invention may also be administered in a similar manner via a SPINHALER ® dispenser. Each capsule to be used in the SPINHALER ® dispenser contains the required amount of a compound of the invention with the remainder of the capsule being a pharmaceutically acceptable carrier. The compounds may also be administered via a liquid aerosol. Using the schemes and procedures outlined herein and above, the following examples were prepared.

Ethyl N-(2-indanyl)glycinate

2-Indanone (25.1 g. 0.19 mol) and glycine ethyl ester hydrochloride (34.5 g, 0.247 mol) were dissolved in absolute ethanol (700 mL) and sodium cyanoborohydride (25.8 g, 0.41 mol) was added in portions to the solution. After addition the mixture was allowed to sit at room temperature overnight. The ethanol was removed under reduced pressure and the residue treated with water and extracted into ethyl acetate. The organic extract was repeatedly washed with saturated aqueous solutions of sodium bicarbonate and sodium chloride before being dried over magnesium sulfate and filtered. After the solvent was concentrated under vacuum an oil remained which was taken up in ether/ethanol (250/50 mL) and cooled by mean of an ice-water bath. Ether which had previously been saturated with anhydrous hydrogen chloride was slowly added to the solution. The precipitated product was filtered and washed with cold ether/ethanol to yield a white solid (21 g) melting at 166°–168° C.

| Analysis calc. for $C_{13}H_{17}NO_2 \times HCl$: | | | |
|---|---|---|---|
| C, 61.03; | H, 7.09; | N, 5.48; | Cl, 13.86. |
| Found: C, 60.82; | H, 7.01; | N, 5.33; | Cl, 13.98. |

N-CBZ-L-Valyl-N-(2-indanyl)glycine ethyl ester

To a solution of CBZ-L-valine (5.0 g, 0.02 mol) in $CH_2Cl_2$ (50 mL) were added 4-dimethylaminopyridine (2.44 g, 0.02 mol), N-(2-indanyl)glycine ethyl ester hydrochloride (5.6 g, 0.02 mol) and 1-(3-dimethylaminopropyl)-3-ethylcarbodiimide hydrochloride (WSCDI) (3.83 g, 0.02 mol). Approximately 20 mL $CH_2Cl_2$ was used to wash the reagents into the reaction flask. After the mixture was stirred overnight the solvent was removed under vacuo and the residue treated with ethyl acetate: 1N HCl (3:1). The separated organic layer was washed with 1N HCl, 5% aqueous $Na_2CO_3$ and saturated aqueous NaCl-solution followed by drying over magnesium sulfate and filtration. After removal of the solvent under reduced pressure an oil (4.3 g) remained, which was purified over silica gel using $CH_2Cl_2$ as eluent. 3.4 g of a colorless oil was collected (Rf: 0.7, silica gel, $CH_2Cl_2:CH_2OH$ 97:3) and used as is for saponification.

N-CBZ-L-Valyl-N-(2-indanyl)glycine

N-CBZ-L-Valyl-N-(2-indanyl)glycine ethyl ester (13.8 g, 0.0305 mol) was dissolved in ethanol (200 mL) and treated with 1N KOH (30 mL) in 5 mL portions. After the mixture was allowed to sit at room temperature overnight, the ethanol was removed under vacuum, and the residue treated with water. The aqueous mixture was washed three times with ethyl acetate and the layers separated. The aqueous layer was acidified to pH 3 with 1N HCl. The product was extracted into ethyl acetate and washed with saturated aqueous NaCl-solution. After drying over $MgSO_4$, filtration and evaporation under reduced pressure afforded the product as a white semi-solid (9.1 g).

| Analysis calc. for $C_{24}H_{28}N_2O_5 \times \frac{1}{2}H_2O$: | | |
|---|---|---|
| C, 66.50; | H, 6.74; | N 6.46; |
| Found: C, 66.82; | H, 6.75; | N 6.17. |

N-CBZ-L-Valyl-N-(2-indanyl)glycyl-N-[3-(1,1,1-trifluoro-4-methyl-2-hydroxypentyl)]amide N-CNZ-L-Valyl-N-(2-indanyl)glycine (4.25 g, 0.01 mol) was dissolved in $CH_2Cl_2$ (60 mL) and 1,1'-carbonyldiimidazole (1.62 g, 0.01 mol) was added. After two hours of stirring at room temperature a suspension of 3-amino-4-methyl-1,1,1-trifluoro-2-pentanol hydrochloride salt (2.1 g, 0.01 mol) and triethylamine (1.0 g, 0.01 mol) in $CH_2Cl_2$ (30 mL) was added. The mixture was allowed to stir overnight and afterwards it was concentrated under vacuum. The remaining residue was treated with ethyl acetate and washed sequentially with 1N HCl, 5% aqueous $Na_2CO_3$ and saturated aqueous NaCL solutions. The organic extract was dried over $MgSO_4$, filtered and evaporated to yield an oil which was purified over silica gel using $CH_2Cl_2:CH_3OH$ 97:3 as eluent. 4.5 g of the title compound was collected as a solid melting at 64°–67° C.

| Analysis calc. for $CO_{30}H_{38}F_3N_3O_5 \times \frac{1}{2}H_2O$: | | | |
|---|---|---|---|
| C, 61.42; | H. 6.70; | N, 7.16; | F 9.72. |
| Found: C, 61.35; | H, 6.80; | N, 7.19; | F 10.10. |

CBZ-L-Valyl-N-(2-inanyl)glycyl-N-[3-(1,1,1-trifluoro-4-methyl-2-oxopentyl)]amide CBZ-L-Valyl-N-(2-indanyl)glycyl-N-[3-(1,1,1-trifluoro-4-methyl-2-hydroxypentyl)]amide (4.3 g, 0.00745 mol) was added to THF (120 mL) followed by Dess-Martin periodinane (9.5 g, 0.0223 mol) in $CH_2Cl_2$ (110 mL). Trifluoro acetic acid (2.55 g, 0.0223 mol) was slowly added and the reaction mixture was allowed to sit at room temperature overnight. The reaction mixture was concentrated under vacuum and the residue was treated with a mixture of ethyl acetate and saturated aqueous solutions of $NaHCO_3$ and $Na_2S_2O_3$. The organic layer was separated and washed repeatedly with solutions of dilute aqueous $NaHCO_3$ and $Na_2S_2O_3$. After a final wash with brine, the organic extract was dried over $MgSO_4$, filtered and evaporated to produce a solid, which was purified over silica gel using a gradient solution with $CH_2Cl_2$ followed by $CH_2Cl_2:CH_3OH$, 97:3.

Yield 3.1 g white solid; mp: 49°–54° C.

| Analysis calc. for $C_{30}H_{36}F_3N_3O_5 \times \frac{1}{2}H_2O$: | | | |
|---|---|---|---|
| C, 61.63; | H, 6.38; | N, 7.19; | F, 9.75. |
| Found: C, 61.42; | H, 6.56; | N, 6.72; | F, 9.73. |

Method A (5S)-2,5-Diisopropyl-3-hydroxy-3-trifluoromethyl-6-oxo-7-(2-indanyl)-2,3-dihydroimidazo[1,2a]piperazine Palladium on carbon 10% (1.0 g) was placed in a round bottom flask and the flask was flushed with nitrogen. N-CBZ-L-Valyl-N-(2-indanyl)glycyl-N-[3-(1,1,1-trifluoro-4-methyl-2-oxopentyl)]amide (1.15 g, 2.0 mmol) in methanol (50 mL) was introduced into the flask followed by cyclohexene (0.33 g, 4.0 mmol). The mixture was immersed into a warm oil bath and refluxed for 15 to 20 minutes. The catalyst was removed by filtration through a bed of Celite diatomaceous earth and the filtrate was evaporated under reduced pressure. The residue was repeatedly treated with a mixture of petroleum ether/diethyl ether and filtered.

Yield 0.8 g; mp;: 58°–63° C.

| Analysis calc. for $C_{22}H_{28}F_3N_3O_2$: | | | |
|---|---|---|---|
| C, 62.40; | H, 6.66; | N, 9.92; | F, 13.46. |
| Found C, 62.11; | H, 6.68; | N. 9.60; | F, 13.32. |

Method B

N-CBZ-L-Valyl-N-(2-indanyl)glycyl-N-[3-(1,1,1-trifluoro-4-methyl-2-oxopentyl)]amide N-CBZ-L-Valyl-N-(2-indanyl)glycyl-N-[3-(1,1,1-trifluoro-4-methyl-2-oxopentyl)]amide (1.0 g, 1.74 mmol) was dissolved in 1,4-dioxane (70 mL). Ether (4 mL), which had previously been saturated with dry hydrogen chloride, and catalytic amounts of palladium on carbon (10%) were added and the mixture was allowed to shake on a Parr Hydrogenator at 45–50 pounds per square inch hydrogen pressure for several hours. The mixture was filtered through a pad of Celite diatomaceous earth and the 1,4-dioxane was removed under reduced pressure. The crude material (0.72 g) was treated with a mixture of petroleum ether/diethyl ether and filtered to yield 0.5 g of the title compound.

Ethyl N-cyclooctyl glycinate

Cyclooctanone (40.4 g, 0.32 mol) and glycine ethyl ester hydrochloride (34.9 g, 0.25 mol) were dissolved in absolute ethanol (750 mL). Sodium cyanoborohydride (33 g, 0.525 mol) was added in portions to the solution. After addition, the mixture was allowed to sit at room temperature overnight. The ethanol was removed under reduced pressure and the residue treated with water and extracted into ethyl acetate. The organic extract was repeatedly washed with saturated solutions of sodium bicarbonate and sodium chloride before being dried over magnesium sulfate and filtered. After the solvent was stripped under vacuum, an oil remained which was taken up in ether/ethanol (250/50 mL) and cooled by means of an ice-water bath. Ether previously saturated with anhydrous hydrogen chloride was slowly added to the solution. The precipitated product was filtered off and washed with cold ether/ethanol to yield a white solid (45.2 g) melting at 156°–159° C.

| Analysis calc. for $C_{12}H_{23}NO_2 \times HCl$: | | |
|---|---|---|
| C, 57.70; | H, 9.68; | N, 5.61. |
| Found: C, 57.74; | H, 9.90; | N, 5.70. |

N-t-BOC-L-Valyl-N-cyclooctyl glycine ethyl ester t-BOC-L-Valine (10.86 g, 0.05 mol) was dissolved in dry $CH_2Cl_2$ (110 mL) and dimethylaminopyridine [(DMAP) 6.1 g 0.05 mol] was added followed by ethyl-N-(cyclooctyl)glycinate hydrochloride (13.74 g, 0.055 mol) and WSCDI (9., 0.05 mol). Following the stirring of the reaction mixture overnight at ambient temperature, the $CH_2Cl_2$ was removed under reduced pressure and the residue treated with ethyl acetate: 1N HCl acid (3:1). The organic extract was washed in the stated order with 1N HCl, dilute aqueous $Na_2CO_3$ and saturated aqueous NaCl solutions. The organic solution was dried over $MgSO_4$ and filtered followed by evaporation under vacuum to yield 14.6 g of an oil which was purified over silica gel using $CH_2Cl_2$:$CH_3OH$, 97:3 as eluent.

Yield: 10.1 g. (Rf: 0.35, silica gel, $CH_2Cl_2$:$CH_3OH$ 97:3).

| Analysis calc. for $C_{22}H_{40}N_2O_5$: | | |
|---|---|---|
| C, 64.05; | H, 9.77; | N, 6.79. |
| Found: C, 64.38; | H, 9.89; | N, 6.87. |

N-t-BOC-L-Valyl-N-cyclooctyl glycine

N-t-BOC-L-Valyl-N-cyclooctyl glycine ethyl ester (9.3 g, 0.0225 mol) was dissolved in ethanol (100 mL) and treated with 1N KOH (20 mL) in portions of 4 mL. After the mixture was allowed to sit at room temperature overnight, the ethanol was removed under vacuum and the residue treated with water. The aqueous mixture was washed three times with ethyl acetate and acidified with 2N HCl. The product was extracted into ethyl acetate and washed with saturated aqueous NaCl. After drying over $MgSO_4$, filtration and evaporation under reduced pressure obtained 6.5 g pure product melting at 63°–38° C.

| Analysis calc. for $C_{20}H_{36}N_2O_5$: | | |
|---|---|---|
| C, 62.47; | H, 9.44; | N, 7.29. |
| Found: C, 62.10; | H, 9.24; | N, 6.97. |

N-t-BOC-L-Valyl-N-cyclooctylglycyl-N-[3-(1,1,1-trifluoro-4-methyl-2-hydrooxypentyl)]amide N-t-BOC-L-Valyl-N-cyclooctylglycine (3.85 g, 1.0mmol) was dissolved in THF (50 mL) and 1,1'-carbonyldiimidazole (1.62 g, 1.0 m) was added. After two hours of stirring at room temperature, a suspension of 3-amino-4-methyl-1,1,1-trifluoro-2-pentanol hydrochloride (2.3 g, 1.1 mmol) and triethylamine (1.1 g, 1.1 mmol) in THF (30 mL) was added. The mixture was allowed to sit overnight, and afterwards it was concentrated under vacuum. The remaining residue was treated with ethyl acetate and washed sequentially with 1N HCl, 5% aqueous $Na_2CO_3$ and saturated aqueous sodium chloride. The organic extract was dried over $MgSO_4$, filtered and evaporated to yield 4.5 g of a solid melting at 67°–74° C.

| Analysis calc. for $C_{26}H_{46}F_3N_3O_5$: | | |
|---|---|---|
| C, 58.08; | H, 8.62; | N, 7.82. |
| Found: C, 57.82; | H, 8.36; | N, 7.71. |

N-t-BOC-L-Valyl-N-cyclooctylglycyl-N-[3-(1,1,1-trifluoro-4-methyl-2-oxopentyl]amide N-t-BOC-L-Valyl-N-cyclooctylglycyl-N-[3-(1,1,1-trifluoro-4-methyl-2-hydroxypentyl)]amide (1.08 g, 2 mmol) was added to $CH_2Cl_2$ (20 mL) followed by Dess-Martin periodinane (2.54 g, 6 mmol) in $CH_2Cl_2$ (35 mL). The reaction mixture was allowed to sit at room temperature overnight. The solvents were evaporated off under vacuum and the residue treated with a mixture of ethyl acetate and saturated aqueous solutions of $NaHCO_3$ and $Na_2S_2O_3$. The organic layer was separated and washed repeatedly with solutions of dilute aqueous $NaHCO_3$ and $Na_2S_2O_3$. After a final wash with brine, the organic extract was dried over $MgSO_4$, filtered and evaporated to afford a solid, which was purified over silica gel using $CH_2Cl_2$:$CH_3OH$ 97:3, as eluent.

Yield 0.65 g of the title compound which was used directly for the next reaction.

(5S)-2,5-Diisopropyl-3-hydroxy-3-trifluoromethyl-6-oxo-7-cyclooctyl-2,3-dihydroimidazo[1.2a]piperazine N-t-BOC-L-Valyl-N-cyclooctylglycyl-N-[3-(1,1,1-trifluoro-4-methyl-2-oxopentyl)]amide (0.41 g, 0.765 mmol) was dissolved in ethyl ether (2 mL) and cooled with an ice bath. Ethyl ether (8 mL) which was previously saturated with dry hydrogen chloride was added. The mixture was allowed to sit at room temperature overnight. The solvents were evaporated off under reduced pressure and the residue was treated with ethyl ether:$CH_2Cl_2$ 1:1 and triethylamine (2 mL). After 2 hours stirring at room temperature, the precipitated triethylamine hydrochloride was filtered off and the solvents evaporated under vacuum. The residue was purified over silica gel using $CH_2Cl_2$:$CH_3OH$ 97:3 as eluent. Collected 0.27 g of mixture of diastereomers melting at 57°–65° C.

| Analysis calc. for $C_{21}H_{34}F_3N_3O_2 \times \frac{1}{2}H_2O$: | | | |
|---|---|---|---|
| C, 59.14; | H, 8.27; | N, 9.85; | F, 13.36. |
| Found: C, 58.94; | H, 7.83; | N, 9.82; | F, 13.60. |

N-t-BOC-Valyl-N-[2-(3,4-dimethoxy)phenethyl]glycine ethyl ester t-BOC-L-Valine (5.9 g, 0.0273 mol) was dissolved in dry THF (50 mL) and 1,1'-carbonyldiimidazole (4.4 g, 0.0273 mol) was added in portions. After the mixture had been stirred at room temperature for one hour, a suspension of ethyl-N-[2-(3,4-dimethoxy)phenethyl]-glycinate hydrochloride (7.2 g, 0.0237 mol) and triethylamine (2.4 g, 0.0237 mol) in THF (30 mL) was added. Following the stirring of the reaction mixture overnight at ambient temperature, the THF was removed under reduced pressure and the residue treated with ethyl acetate:1N HCl acid (3:1). The organic extract was washed in the following order with 1N HCl, dilute aqueous $Na_2CO_3$ and saturated aqueous NaCl solutions. The organic solution was dried over $MgSO_4$ and filtered, followed by evaporation under vacuum to yield an oil (2.3 g), Rf: 0.75, silica gel, $CH_2Cl_2$:$CH_3OH$ 97:3) which was used as is for the next step.

N-t-BOC-L-Valyl-N-[2-(3,4-dimethoxy)phenethyl]glycine

N-t-BOC-L-Valyl-N-[2-(3,4-dimethoxy)phenethyl]glycine ethyl ester (3.3 g, 7.07 mmol) was dissolved in ethanol (45 mL) and treated with 1N KOH (7.0 mL) in portions of 1.5 mL. After the mixture was allowed to sit at room temperature overnight, the ethanol was removed under vacuum and the residue treated with water. The aqueous mixture was washed three times with ethyl acetate and the layers separated. The aqueous layer was acidified with diluted HCl. The product was extracted into ethyl acetate and washed with saturated aqueous NaCl. After drying over $MgSO_4$, filtration and evaporation under reduced pressure obtained the product as a white semi-solid (2.4 g). The product was used directly for the next reaction.

N-t-BOC-L-Valyl-N-[2-(3,4-dimethoxy)phenethyl]glycyl-N-[3-(1,1,1-trifluoro-4-methyl-2-hydroxypentyl)]amide N-t-BOC-L-Valyl-N-[2-(3,4-dimethoxy)phenethyl]glycine (2.4 g, 5.47 mmol) was dissolved in $CH_2Cl_2$ (40 mL) and 1,1'-carbonyldiimidazole (0.89 g, 5.47 mmol) was added. After two hours of stirring at room temperature, a solution of 3-amino-4-methyl-1,1,1-trifluoro-2-pentanol (1.03 g, 6.02 mmol) in $CH_2Cl_2$ (20 mL) was added. This mixture was allowed to sit overnight and afterwards it was concentrated under vacuum. The remaining residue was treated with ethyl acetate and washed sequentially with 1N HCl, 5% aqueous $Na_2CO_3$ and saturated aqueous sodium chloride. The organic extract was dried over $MgSO_4$, filtered and evaporated to yield 1.6 g of an amorphous solid melting at 46°–53° C. The product was used as is for the next reaction.

| Analysis calc. for $C_{28}H_{44}F_3N_3O_7$: | | | |
|---|---|---|---|
| C, 56.84; | H, 7.50; | N, 7.10; | F, 9.63. |
| Found: C, 56.64; | H, 7.63; | N, 7.13; | F, 9.72. |

N-t-BOC-L-Valyl-N-[(2-(3,4-dimethoxy)phenethyl]glycyl-N-[3-(1,1,1-trifluoro-4-methyl-2-oxopentyl)]amide N-t-BOC-L-Valyl-N-[2-(3,4-dimethoxy)phenethyl]glycyl-N-[3-(1,1,1-trifluoro-4-methyl-2-oxopentyl)]amide (1.6 g, 2.7 mmol) was added to $CH_2Cl_2$ (25 mL) followed by Dess-Martin periodinane (3.44 g, 8.11 mmol) in $CH_2Cl_2$ (35 mL). The reaction mixture was allowed to sit at room temperature overnight. The solvents were evaporated off under vacuum and the residue treated with a mixture of ethyl acetate and saturated aqueous solutions of $NaHCO_3$ and $Na_2S_2O_3$. The organic layer was separated and washed repeatedly with solutions of dilute aqueous $NaHCO_3$ and $Na_2S_2O_3$. After a final wash with brine, the organic extract was dried over $MgSO_4$, filtered and evaporated to afford a solid, which was purified over silica gel using $CH_2Cl_2$:$CH_3OH$ 99:1, as eluent. Yield 1.1 g of a sticky compound which was used as is for the next reaction.

(5S)-2,5-Diisopropyl-3-hydroxy-3-trifluoromethyl-6-oxo-7-[2-(3,4-dimethoxy)phenethyl]-2,3-dihydroimidazo[1.2a]piperazine N-t-BOC-L-Vayl-N-[2-(3,4-dimethoxy)phenethyl]glycyl-N-[3-(1,1,1-trifluoro-4-methyl-2-oxopentyl)]amide (1.0 g, 1.7 mmol) was dissolved in ethyl ether (4 mL) and cooled with an ice bath. Ethyl ether (8 mL) which was previously saturated with dry hydrogen chloride was added. The mixture was allowed to sit at room temperature overnight. The solvents were evaporated off under reduced pressure, and the residue was treated with ethyl ether:$CH_2Cl_2$ 1:1 and triethylamine (2 mL). After 2 hours at room temperature, the precipitated triethylamine hydrochloride was filtered off and the solvents evaporated under vacuum. The residue was purified over silica gel using $CH_2Cl_2$:$CH_3OH$ 97:3 as eluent. 0.7 g of a hygroscopic mixture of a diastereoisomers was collected, melting at 38°–46° C.

| Analysis calc. for $C_{23}H_{32}F_3N_3O_4 \times 1\frac{1}{4}H_2O$: | | |
|---|---|---|
| C, 55.41; | H, 7.08; | N, 8.43. |
| Found: C, 55.47; | H, 6.74; | N, 8.15. |

Using appropriate starting materials and analogous procedures to those described above, the following compounds were prepared:

(5S,11S)-(2,5-Diisopropyl-3-hydroxy-6-oxo-3-trifluoromethyl)-2,3-dihydroimidazo[1,2-a]pyyrrolo[2,1-c]piperazine -continued

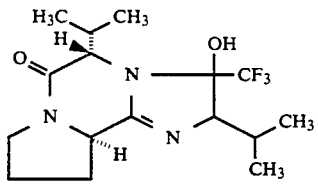

(5S)-[2,5-Diisopropyl-7-[(1S)-(ethoxycarbonyl)ethyl]-3-hydroxy-6-oxo-3-trifluoromethyl]-2,3-dihydroimidazo-[1,2-a]piperazine

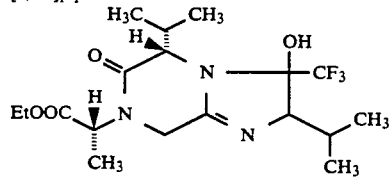

(5S,8S)-[3-Hydroxy-2-isobutyl-5-isopropyl-8-methyl-6-oxo-3-trifluoromethyl-7-(benzyl)]-2,3-dihydroimidazo-[1,2-a]piperazine

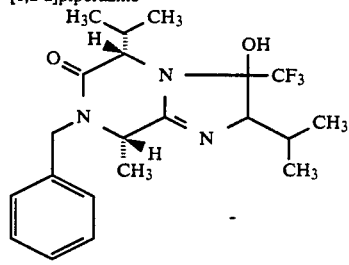

(5S,11R)-[2,5-Diisopropyl-6,9-dioxo-3-hydroxy-3-trifluoromethyl]-2,3-dihydroimidazo[1,2-a]thiazolidinao-[4,3-c]piperazine

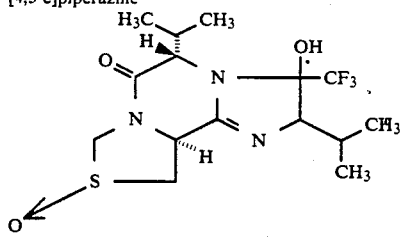

(5S)-[2,5-Diisopropyl-3-hydroxy-6-oxo-3-trifluoromethyl-7-(N-carbobenzyloxy-L-alanyl)]-2,3-dihydroimidazo-[1,2-a]piperazine

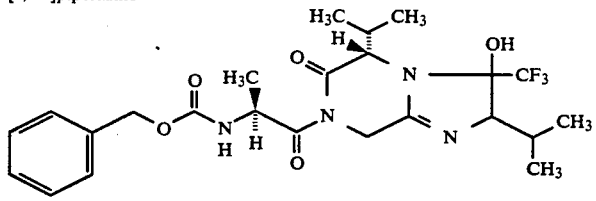

(5S)-[2,5-Diisopropyl-3-hydroxy-6-oxo-3-trifluoromethyl-7-[[4-[(4-bromophenyl)sulfonylaminocarbonyl]benzoyl]-N-(2-aminoethyl)]]-2,3-dihydroimidazo[1,2-a]piperazine

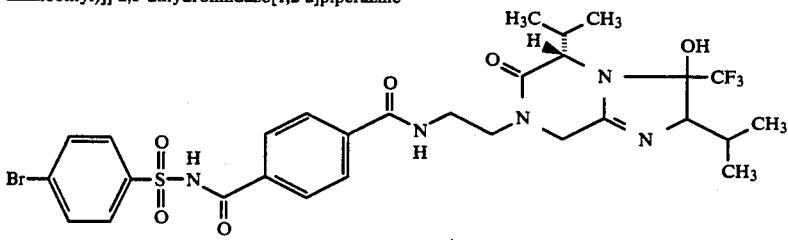

(5S)-[2,5-Diisopropyl-3-hydroxy-6-oxo-3-trifluoromethyl-7-

(3-pyridinylmethyl)]-2,3-dihydroimidazo[1,2-a]piperazine

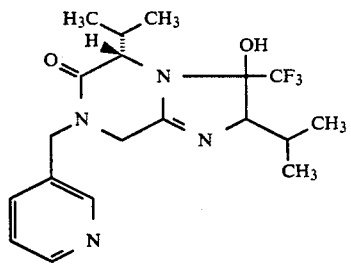

(5S)-[2,5-Diisopropyl-7-furfuryl-3-hydroxy-6-oxo-3-trifluoromethyl]-2,3-dihydroimidazo[1,2-a]piperazine

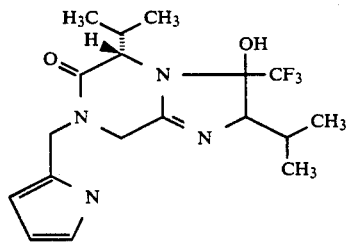

(5S,11S)-[6,9-Dioxo-3-hydroxy-2-isopropyl-5-methyl-3-trifluoromethyl]-2,3-dihydroimidazo[1,2-a]pyrrolo[2,1-c]-piperazine

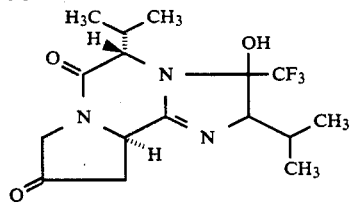

(5S)-[2,5-Diisopropyl-3-hydroxy-6-oxo-3-trifluoromethyl-7-[N-(methylsuccinyl)-L-alanyl]]-2,3-dihydroimidazo-[1,2-a]piperazine

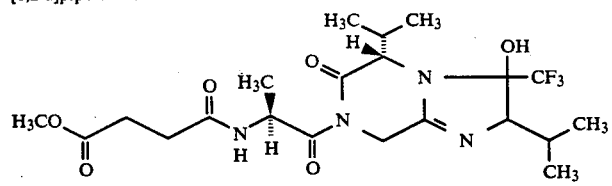

(5S),14S)-[2,5-Diisopropyl-3-hydroxy-6-oxo-3-trifluoromethyl]-2,3-dihydroimidazo[1,2-a]-7,8,13,14-tetrahydroisoquinolino[3,2-c]piperazine

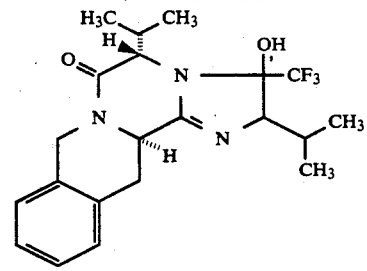

(5S)-[7-(exo-Bicyclo[2.2.1]hept-2-yl)-2,5-diisopropyl-3-hydroxy-6-oxo-3-trifluoromethyl]-2,3-dihydroimidazo-[1,2-a]piperazine

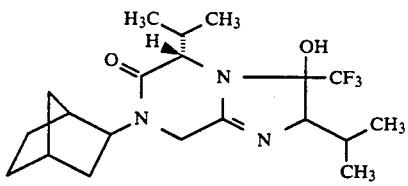

(5S)-[3-Hydroxy-2-isopropyl-6-oxo-5-methyl-3-trifluoromethyl-7-[4-[(4-bromophenyl)sulfonyl-aminocarbonyl]phenyl]]-2,3-dihydroimidazo[1,2-a]piperazine

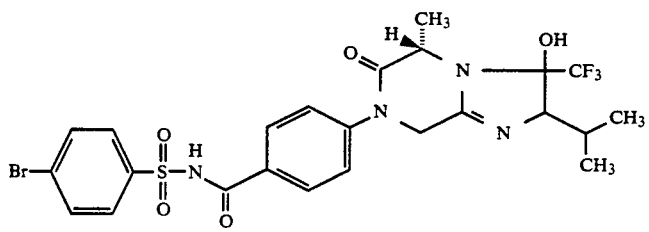

(5S)-[3-Hydroxy-6-oxo-3-trifluoromethyl-2,5,8-triisopropyl]-2-3-dihydroimidazo[1,2-a]piperazine

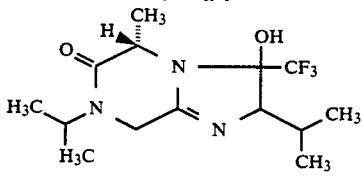

(5S)-[3-Hydroxy-2-isopropyl-5-methyl-6-oxo-3-trifluoromethyl-7-[3-(2-ethoxycarbonyl)ethylamino-carbonyl]cyclohexyl]-2,3-dihydroimidazo[1,2-a]piperazine

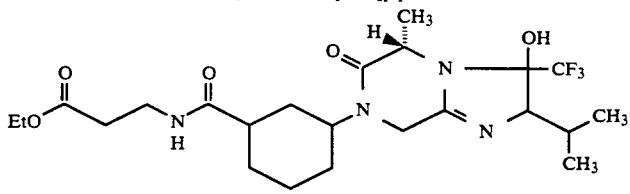

(5S)-[7-(n-Hexyl)-3-hydroxy-2-isopropyl-5-methyl-3-trifluoromethyl]-2,3-dihydroimidazo[1,2-a]piperazine

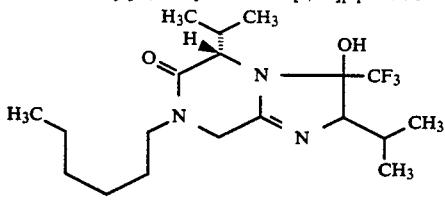

(2S, 5S)-[3-(Ethyl 2,2-difluoromethylcarboxylate)-2,5-diisopropyl-3-hydroxy-7-(2,3-dihydro-1H-inden-2-yl)]-2,3-dihydroimidazo[1,2-a]piperazine

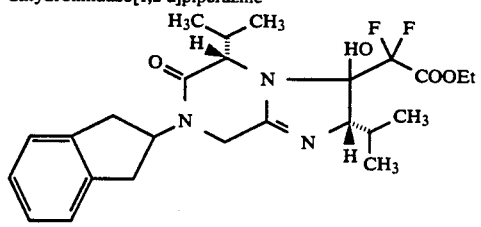

(5S)-[7-Cyclohexyl-2,5-diisopropyl-3-hydroxy-3-(para-trifluoromethyl)phenyl]-2,3-dihydroimidazo[1,2-a]piperazine

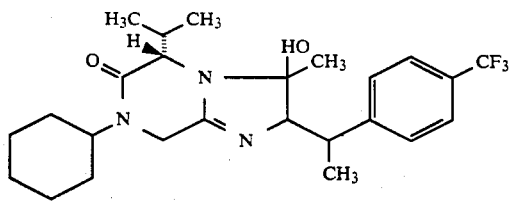

(5S)-[7-[1-(N-Carbobenzyloxy-L-alanyl)piperidin-4-yl]-2,5-diisopropyl-3-hydroxy-6-oxo-3-trifluoromethyl]-2,3-dihydroimidazo[1,2-a]piperazine

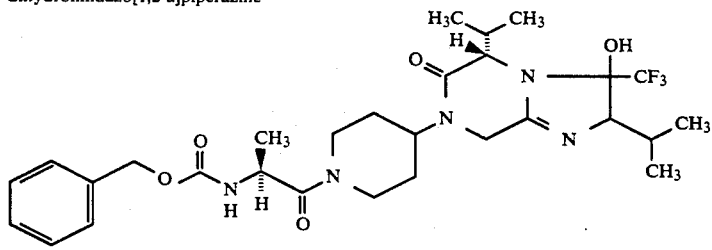

(2S, 5S)-[3-(Ethyl 2,2-difluoromethylcarboxylate)-2,5-diisopropyl-3-hydroxy-7-[[4-[(4-bromophenyl)sulfonylaminocarbonyl]benzoyl]-N-((2S)-aminopropyl)]]-2,3-dihydroimidazo-[1,2-a]piperazine

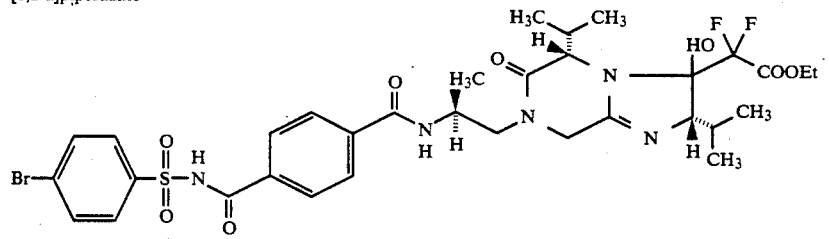

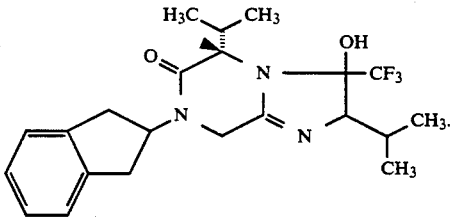

What is claimed is:
1. A compound of formula:

2. A method of treating disease in human caused by human neutrophil elastase which comprises administering to the human afflicted therewith an effective amount of a compound as recited in claim 1.

* * * * *